United States Patent
Yu et al.

(10) Patent No.: US 10,601,046 B2
(45) Date of Patent: Mar. 24, 2020

(54) MODIFICATION OF LITHIUM TITANATE ELECTRODE PARTICLES TO ELIMINATE GAS FORMATION IN CELL OPERATION

(71) Applicant: GM GLOBAL TECHNOLOGY OPERATIONS LLC, Detroit, MI (US)

(72) Inventors: Zhiqiang Yu, Shanghai (CN); Haijing Liu, Shanghai (CN)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 15/761,877

(22) PCT Filed: Oct. 7, 2015

(86) PCT No.: PCT/CN2015/091426
§ 371 (c)(1),
(2) Date: Mar. 21, 2018

(87) PCT Pub. No.: WO2017/059560
PCT Pub. Date: Apr. 13, 2017

(65) Prior Publication Data
US 2018/0287156 A1    Oct. 4, 2018

(51) Int. Cl.
*H01M 4/60* (2006.01)
*H01M 10/0525* (2010.01)
(Continued)

(52) U.S. Cl.
CPC ............ *H01M 4/60* (2013.01); *C01G 23/005* (2013.01); *C07F 7/003* (2013.01); *C09C 1/36* (2013.01);
(Continued)

(58) Field of Classification Search
CPC ......... C07F 7/003; C09C 1/36; C09C 1/3684; C01G 23/005; H01M 4/485; H01M 2220/20; H01M 4/60
See application file for complete search history.

(56) References Cited

U.S. PATENT DOCUMENTS 6,420,456 B1 *   7/2002   Koski .................. C08K 9/06
                                            106/490
2008/0158784 A1 *  7/2008   Hwang .............. H01G 9/0032
                                            361/529

(Continued)

FOREIGN PATENT DOCUMENTS

CN       103187562 A       7/2013
CN       103500817 A   *   1/2014
CN       103904332 A       7/2014

OTHER PUBLICATIONS

Machine translatin of CN-103904332-A, publication date Jul. 2014.*

(Continued)

*Primary Examiner* — Jun Li
(74) *Attorney, Agent, or Firm* — Reising Ethington P.C.

(57) ABSTRACT

Lithium titanate, $Li_4Ti_5O_{12}$, particles containing surface hydroxyl groups are susceptible to unwanted gas generation (such as hydrogen) in the presence of water contamination when the particles are used as active anode electrode material in lithium-ion cells operating with an anhydrous liquid electrolyte. In accordance with this disclosure, the hydroxyl groups on the surfaces of the particles are reacted with one of a group of selected agents containing organic alkoxy groups to form hydrophobic moieties on the surfaces of the particles which effectively block water molecules from the surfaces of lithium titanate particles in the anode of the cell.

20 Claims, 3 Drawing Sheets

(51) Int. Cl.
  *C09C 1/36* (2006.01)
  *C07F 7/00* (2006.01)
  *C01G 23/00* (2006.01)
  *H01M 4/485* (2010.01)

(52) U.S. Cl.
  CPC .......... *C09C 1/3684* (2013.01); *H01M 4/485* (2013.01); *H01M 10/0525* (2013.01); *H01M 2220/20* (2013.01); *Y02E 60/122* (2013.01)

(56) References Cited

U.S. PATENT DOCUMENTS

| | | | |
|---|---|---|---|
| 2008/0260664 A1* | 10/2008 | Walenzyk | A61K 8/0283 424/60 |
| 2009/0035605 A1* | 2/2009 | Yamamoto | B82Y 30/00 428/702 |
| 2010/0015437 A1* | 1/2010 | Grothe | C08K 9/02 428/329 |
| 2014/0113197 A1 | 4/2014 | Xiao et al. | |
| 2014/0252267 A1 | 9/2014 | Yan et al. | |
| 2015/0083417 A1* | 3/2015 | Lant | C09K 8/58 166/300 |

OTHER PUBLICATIONS

International Search Report and Written Opinion for application No. PCT/CN2015/091426, dated Jul. 8, 2016; 11 pages.

\* cited by examiner

MODIFICATION OF LITHIUM TITANATE ELECTRODE PARTICLES TO ELIMINATE GAS FORMATION IN CELL OPERATION

TECHNICAL FIELD

This disclosure pertains to the modification of the surfaces of small particles of lithium titanate (nominally, $Li_4Ti_5O_{12}$, sometimes abbreviated as LTO) in preparation for their use as active electrode material in a lithium-ion cell or related electrochemical cell in which LTO-based anodes are combined with a suitable cathode material. The preparatory coating or modification process is performed on LTO particles which have been exposed to moisture and carry many hydroxyl groups (OH groups) bonded to and substantially covering the surfaces of the titanium-containing particles. The selected coating material is reactive with the bonded hydroxyl groups to replace them and to form bonded hydrophobic organic groups that thereafter inhibit any water formed in an operating lithium cell from reacting with the surfaces of the active electrode particles and generating unwanted gas in the electrochemical cell.

BACKGROUND OF THE INVENTION

The material presented as background information in this section of the specification is not necessarily prior art.

Assemblies of lithium-ion battery cells are finding increasing applications in providing motive power in automotive vehicles and in many other commercial applications requiring low weight, highly-efficient electrical power sources. Lithium-sulfur cells and other lithium-electrode containing cells, utilized with anhydrous electrolytes, are also candidates for such applications.

Each lithium-ion cell of the battery is capable of providing an electrical potential of about three to four volts and a direct electrical current based on the composition and mass of the electrode materials in the cell. The cell is capable of being discharged and re-charged over many cycles. A battery is assembled for an application by combining a suitable number of individual cells in a combination of electrical parallel and series connections to satisfy voltage and current requirements for a specified electric motor or other application. In a lithium-ion battery application for an electrically powered vehicle, the assembled battery may, for example, comprise up to three hundred individually packaged cells that are electrically interconnected to provide forty to four hundred volts and sufficient electrical power to an electrical traction motor to drive a vehicle. The direct current produced by the battery may be converted into an alternating current for more efficient motor operation.

The batteries may be used as the sole motive power source for electric motor-driven electric vehicles or as a contributing power source in various types of hybrid vehicles, powered by a combination of an electric motor(s) and a hydrocarbon-fueled engine.

In these automotive applications, each lithium-ion cell typically comprises a negative electrode layer (anode, during cell discharge), a positive electrode layer (cathode, during cell discharge), a thin porous separator layer interposed in face-to-face contact between parallel facing electrode layers, and a lithium-containing, anhydrous liquid, electrolyte solution filling the pores of the separator and contacting the facing surfaces of the electrode layers for transport of lithium ions during repeated cell discharging and re-charging cycles. Each electrode is prepared to contain a layer of an electrode material, typically deposited on a thin layer of a metallic current collector.

For example, the negative electrode material has been formed by depositing a thin layer of graphite or lithium titanate particles, often mixed with conductive carbon black, and a suitable polymeric binder onto one or both sides of a thin foil of copper which serves as the current collector for the negative electrode. The positive electrode also comprises a thin layer of resin-bonded, porous particulate, lithium-metal-oxide composition bonded to a thin foil of aluminum which serves as the current collector for the positive electrode. Thus, the respective electrodes have been made by dispersing mixtures of the respective binders and active particulate materials in a suitable liquid, depositing the liquid-solid mixture as a layer of controlled thickness on the surface of a current collector foil, and drying, pressing, and fixing the resin-bonded electrode particles to their respective current collector surfaces. The positive and negative electrodes may be formed on current collector sheets of a suitable area and shape, and cut (if necessary) and folded or otherwise shaped for assembly into lithium-ion cell containers with suitable porous separators and a liquid electrolyte.

LTO desirably has certain advantages, like high cut voltage (e.g., cut-off potentials relative to a lithium metal reference potential) that desirably minimizes or avoids undesirable coatings of solid electrolyte formation. Furthermore LTO is a zero-strain material having minimal volumetric change during lithium insertion and de-insertion, thus enabling long term cycling stability, high current efficiency, and high rate capabilities. Such long term cycling stability, high current efficiency, and high rate capabilities are particularly advantageous for power battery and start-stop battery use.

However, while LTO is a promising anode material for high power lithium-ion batteries, providing extremely long life and exceptional tolerance to overcharge and thermal abuse, in certain circumstances, when used with certain cathode materials and electrolytes, LTO may potentially have certain disadvantages. For example, it has been observed that the $Li_4Ti_5O_{12}$ particles can interact with incidental water molecules in an operating lithium cell and generate gas within a battery cell. The gas may comprise any of hydrogen, carbon monoxide, carbon dioxide, and gaseous hydrocarbons. It would be desirable to improve LTO anode materials to suppress gas formation, while employing the desirable aspects of the LTO material that provide durable batteries with sustained high capacity, high discharge rates, and long life.

SUMMARY

Lithium titanate ($Li_{4+x}Ti_5O_{12}$ where $0 \leq x \leq 5$) is a crystalline compound that has demonstrated utility as an active anode material for use in lithium-ion cells and other lithium electrochemical cells comprising particles which intercalate lithium ions during cell-charging and release (de-intercalate) lithium ions as the cell is being discharged and producing an electrical current through an external load. In its uncharged state, lithium titanate may be represented by $Li_4Ti_5O_{12}$ (where x is zero). As the electrode material is being charged and is being intercalated with lithium ions, the lithium content of the lithium titanate crystals increases to higher values of x. For example, modified crystal structures corresponding to $Li_7Ti_5O_{12}$ and $Li_9Ti_5O_{12}$ may be formed. When the cell is being discharged to power an external load, lithium atoms yield electrons to an external circuit and lithium ions leave the cell (lithium de-intercalation) and the value of x is progressively reduced toward a value of zero. The abbreviation, LTO, and the name, lithium titanate, are used herein to refer generally to $Li_{4+x}Ti_5O_{12}$ depending on its lithium ion content in the context of the discussion.

The relatively high titanium and oxygen content of LTO is recognized. As described, LTO particles consist of crystals and the crystals are exposed at surfaces of the particles of candidate electrode materials. Water molecules are easily loosely adsorbed onto the particle surfaces. In addition, water molecules can react with titanium atoms on the surfaces of the LTO powder to form attached pendant hydroxyl groups (—OH) and with nearby oxygen atoms to form attached hydrogen atoms.

Lithium-based electrochemical cells are typically organized, constructed, and operated to minimize water contamination as well as the formation of water molecules in the operation of the cell. However, some water molecules may be formed or carried in the anhydrous electrolyte solution during the operation of the cell, and it is found that the surfaces of LTO particles are very capable of both physically adsorbing water molecules and chemically reacting with water molecules to release hydrogen gas and to form pendant hydroxyl groups on the surfaces of the LTO particles which may be further reactive in gas generation in a lithium electrode. Since the electrolyte often contains fluorine or other halogens, other gas compositions may be formed and released from the surfaces of the LTO particles.

In accordance with practices of this disclosure, substantially pure LTO particles are obtained or prepared in a size range and with shapes for use as an active electrode material in the anode of an intended lithium-ion cell or other lithium cell. Often LTO particles are mixed with particles of an electrically conductive material, such as a conductive carbon black, and with an anhydrous solution or dispersion of an organic polymer binder, such as polyvinylidene difluoride, to form a slurry of particles and dissolved resin for deposition of a suitable electrode layer on a current collector (e.g., a copper foil or sheet). Accordingly, for example, the initial LTO particles may be generally spherical in shape and having a suitable size range, typically within an overall range from 50 nanometers to 50 micrometers in diameter or largest dimension. But the surfaces of these initial LTO particles contain adsorbed water molecules and pendant hydroxyl groups resulting from contact of atmospheric water with the substantial area provided by the particle surfaces.

The surfaces of a volume of LTO starting material particles are initially exposed to and reacted with compounds containing organic oxy-alkane groups (or the like) that are reactive with hydroxyl groups (—OH groups) on the surfaces of the LTO particles. The selected compounds react to leave molecules or ions with pendant hydrophobic oxy-alkane-containing groups extending from (and thereby covering or modifying) the surfaces of the LTO particles.

Such compounds producing pendant hydrophobic groups, covering LTO particle surfaces, are characterized by lower organic alcohols (suitably, aliphatic alcohols) or by the presence of organic alkyl or alkoxy groups and hydroxyl groups attached to a central silicon atom, a sulfur atom, or a titanium atom. Each of the specified hydrophobic compounds are capable of reacting with the surface hydroxyl groups (believed to be bonded to titanium atoms in surface crystals of the LTO particles) and thereby substantially covering the surfaces of the LTO particles with pendant hydrophobic groups to thereafter prevent reaction with water molecules when the modified or coated LTO particles have been incorporated in electrodes for a lithium-ion cell or the like. Depending on the composition and the physical state of the applied material, the treating compound may be applied directly to the surfaces of a working volume of the LTO particles. Or a suitable non-aqueous solution of the material may be used in forming the coating of hydrophobic material. As stated, several different types of compounds can be used in the coating or surface modification processes. These groups of compounds will be summarized in this section of the specification, and illustrations of the coating processes will be presented in the Description of Preferred Embodiments.

Simple organic alcohols constitute a first group of compounds that are reactive with surface hydroxyl groups on the surfaces of small LTO particles and of further coating or modifying the particles. Aliphatic alcohols such as methanol, ethanol, propyl and butyl alcohols (R—OH compounds) are suitable for reaction as a liquid or vapor with surface hydroxyl groups on the LTO particles. Higher molecular weight alcohols may be used, but the lower molecular weight alcohols are often suitable. Water is formed by reaction with the alcohol with the surface hydroxyl groups, and the water is released from the LTO particles. The resulting pendant alkoxy groups (—OR) provide a protective hydrophobic covering or coating on the surfaces of the particles. The alkoxy groups remain on the surfaces of the particles as the particles are resin-bonded and formed as a porous electrode layer on the surface of a suitable current collector membrane or the like.

A second group of suitable R—OH group-containing reactive compounds comprise sulfenic acid compounds (R—S—OH), sulfinic acid (R—SO—(OH)) compounds, and sulfonic acid (R—S(=$O_2$)—OH) compounds. Suitable R groups for this group of sulfur-containing compounds include alkane groups, aromatic groups, and alkyl amino groups.

A third group of reactive compounds include silane coupling agents characterized by the formula $Y_{4-a}Si(OX)_a$, where a has a value of 1-3, where X and Y may be alkyl groups selected such that one alkoxy group (OX) reacts with a hydroxyl group on the surface of a LTO particle and the remaining OX and Y groups serve to block water molecules from access to the surface of the particle.

A fourth group of reactive compounds include suitable titanate coupling agents characterized by the formula, $Ti(OR)_4$ where R is a suitable alkane. The alkane group is selected such that at least one OR group reacts with a hydroxyl group on the surface of a LTO particle and the remaining OR groups attached to the titanium atom serve as hydrophobic groups to block water molecules from access to the surface of the LTO particle.

A volume of LTO particles (with their surface-coating hydroxyl groups) is exposed and reacted with a sufficient quantity of one of these groups of compounds so as to consume substantially all of the OH groups, typically removing them as water or as an alkanol. The OH groups are thus utilized and replaced with many pendant hydrophobic organic groups that serve to block water molecules from the surface of each LTO particle when the particles are subsequently organized as an electrode material layer in a lithium-ion cell or other cell utilizing LTO particles as an electrode material.

Illustrations of such surface modification processes for LTO particles are presented below in this specification.

DESCRIPTION OF PREFERRED EMBODIMENTS

An active lithium-ion cell material is an element or compound which accepts or intercalates lithium ions, or releases or gives up lithium ions in the discharging and re-charging cycling of the cell. A few examples of suitable electrode materials for the anode electrode (negative electrode) of a lithium ion cell are graphite, silicon, alloys of silicon with lithium or tin, silicon oxides ($SiO_x$), and lithium titanate. During cell-discharge, electrons are released from the anode material into the electrical power-requiring external circuit and lithium ions are released (de-intercalated) into an anhydrous electrolyte. Lithium titanate is a preferred anode material and it is the coating of particles of lithium titanate which is the focus of the coating practices of this invention.

Examples of positive electrode materials (cathode) include lithium manganese oxide, lithium nickel oxide, lithium cobalt oxide and other lithium-metal-oxides. Other materials are known and commercially available. One or more of these materials may be used in an electrode layer. In accordance with practices of this invention the respective electrode materials are typically initially in the form of submicron to micron-size particles, in the range of tens of nanometers to tens of microns.

Figure 1:
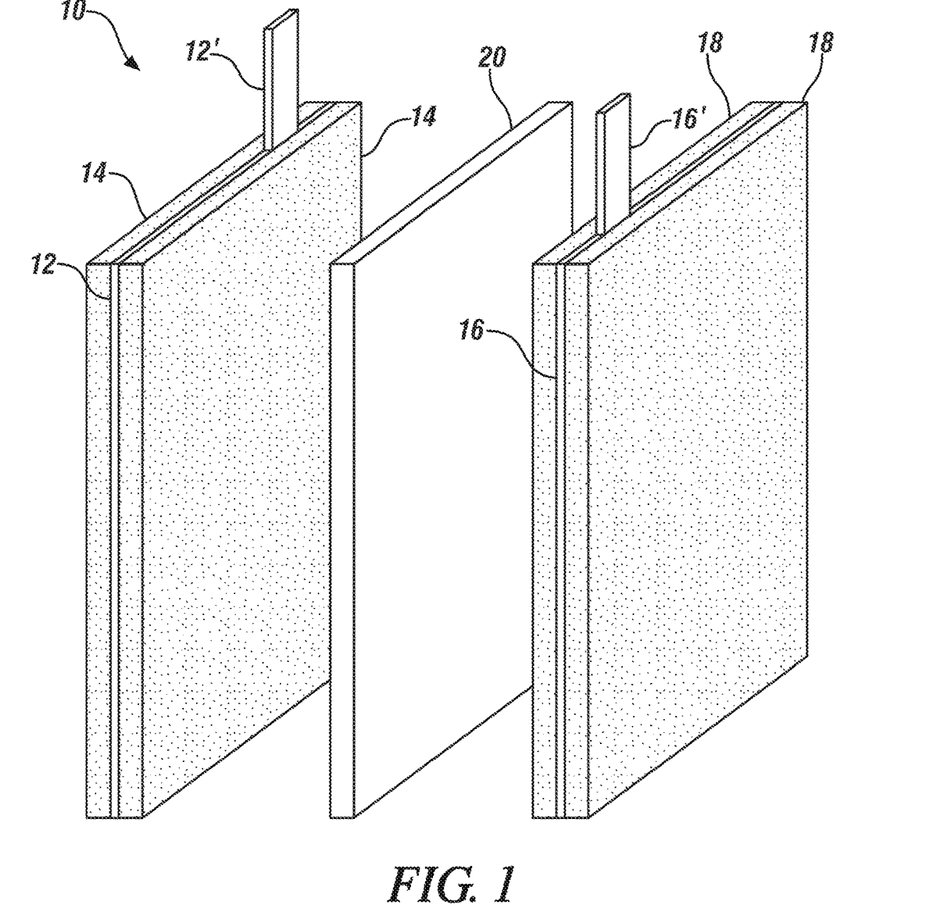
FIG. 1 is an enlarged schematic illustration of a spaced-apart assembly of three solid members of a lithium-ion electrochemical cell. The three solid members are spaced apart in this illustration to better show their structure. The illustration does not include an electrolyte solution whose composition and function will be described in more detail below in this specification.

FIG. 1 is an enlarged schematic illustration of a spaced-apart assembly 10 of three solid members of a lithium-ion electrochemical cell. The three solid members are spaced apart in this illustration to better show their structure. The illustration does not include an electrolyte solution whose composition and function will be described in more detail below in this specification.

In FIG. 1, a negative electrode consists of a relatively thin, conductive metal foil current collector 12. The negative electrode current collector 12 is typically formed of a thin layer of copper. The thickness of the metal foil current collector is suitably in the range of about ten to twenty-five micrometers. The current collector 12 has a desired two-dimensional plan-view shape for assembly with other solid members of a cell. Current collector 12 is illustrated as having a major surface with a rectangular shape, and further provided with a connector tab 12' for connection with other electrodes in a grouping of lithium-ion cells to provide a desired electrical potential or electrical current flow.

Deposited on both major faces of the negative electrode current collector 12 are thin, porous layers of negative electrode material 14. In accordance with this disclosure, the negative electrode material is typically resin-bonded particles of lithium titanate which may include interspersed carbon particles providing enhanced electron conductivity. As illustrated in FIG. 1, the layers of negative electrode material 14 are typically co-extensive in shape and area with the main surface of their current collector 12. The particulate electrode material has sufficient porosity to be infiltrated by a liquid, non-aqueous, lithium-ion containing electrolyte. In accordance with embodiments of this invention, the thickness of the rectangular layers of LTO-containing negative electrode material may be up to about two hundred micrometers so as to provide a desired current and power capacity for the negative electrode.

A positive electrode is shown, comprising a positive current collector foil 16 and, on each major face, a coextensive, overlying, porous deposit of resin-bonded, particulate, positive electrode material 18. Positive current collector foil 16 also has a connector tab 16' for electrical connection with other electrodes in a grouping of lithium-ion cells or with other electrodes in other cells that may be packaged together in the assembly of a lithium-ion battery. The positive current collector foil 16 and its opposing coatings of porous positive electrode material 18 are typically formed in a size and shape that are complementary to the dimensions of an associated negative electrode. In the illustration of FIG. 1, the two electrodes are identical in their shapes and assembled in a lithium-ion cell with a major outer surface of the negative electrode material 14 facing a major outer surface of the positive electrode material 18. The thicknesses of the rectangular positive current collector foil 16 and the rectangular layer of positive electrode material 18 are typically determined to complement the negative electrode material 14 in producing the intended electrochemical capacity of the lithium-ion cell. The thicknesses of current collector foils are typically in the range of about 10 to 25 micrometers. And the thicknesses of the respective electrode materials are typically up to about 200 micrometers.

A thin porous separator layer 20 is interposed between a major outer face of the negative electrode material layer 14 (as illustrated in FIG. 1) and a major outer face of the positive electrode material layer 18. A like separator layer 20 could also be placed against each of the opposite outer layer of negative electrode material 14 and the opposite outer layer of positive electrode material 18 if the illustrated individual cell assembly 10 is to be combined with like assemblies of cell members to form a battery with many cells.

In many battery constructions, the separator material is a porous layer of a polyolefin, such as polyethylene (PE) or polypropylene (PP). Often the thermoplastic material comprises inter-bonded, randomly oriented fibers of PE or PP. The fiber surfaces of the separator may be coated with particles of alumina, or other insulator material, to enhance the electrical resistance of the separator, while retaining the porosity of the separator layer for infiltration with liquid electrolyte and transport of lithium ions between the cell electrodes. The separator layer 20 is used to prevent direct electrical contact between the facing negative and positive electrode material layers 14, 18, and is shaped and sized to serve this function. In the assembly of the cell, the facing major faces of the electrode material layers 14, 18 are pressed against the major area faces of the separator membrane 20. A liquid electrolyte is typically injected into the pores of the separator and electrode material layers.

The electrolyte for the lithium-ion cell is often a lithium salt dissolved in one or more organic liquid solvents. Examples of suitable salts include lithium hexafluorophosphate ($LiPF_6$), lithium tetrafluoroborate ($LiBF_4$), lithium perchlorate ($LiClO_4$), lithium hexafluoroarsenate ($LiAsF_6$), and lithium trifluoroethanesulfonimide. Some examples of solvents that may be used to dissolve the electrolyte salt include ethylene carbonate, dimethyl carbonate, methylethyl carbonate, propylene carbonate. There are other lithium salts that may be used and other solvents. But a combination of lithium salt and solvent is selected for providing suitable mobility and transport of lithium ions in the operation of the cell. The electrolyte is carefully dispersed into and between closely spaced layers of the electrode elements and separator layers. The electrolyte is not illustrated in the drawing figure because it is difficult to illustrate between tightly compacted electrode layers.

In accordance with practices of this invention, lithium titanate particles are prepared by a surface modification process for use as an anode material in a lithium-ion cell and other lithium cells.

Preparation of Lithium Titanate Particles as Non-Gassing Electrode Material.

As summarized above in this specification, lithium titanate particles, intended for use as anode materials in lithium cells, are contacted with a selected material which is used to react with hydroxyl groups on the surfaces of the particles to form pendant water-repelling oxy-alkane groups or other suitable hydrophobic organic groups.

Treatment of the LTO Particles with an Alkanol.

Figure 2:
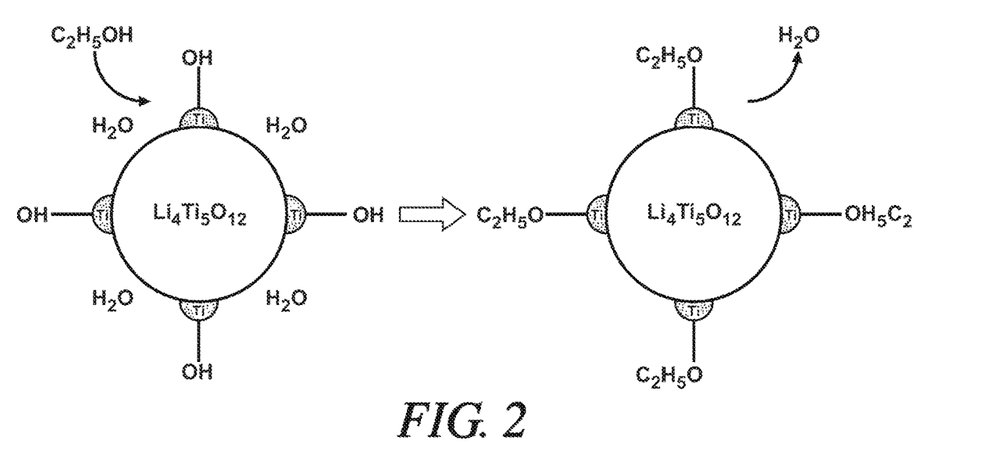
FIG. 2 is an enlarged schematic illustration of the chemical treatment of the surface of a powder particle of lithium titanate with ethanol to form pendant ethoxy groups at a few schematically-illustrated OH sites on titanium atoms on the surface of the powder particle. The surface of each LTO particle actually contains many OH groups, chemically bonded to titanium atoms, and the OH groups react with ethanol to release water and to form many pendant ethoxy groups. When such treated lithium titanate powder is employed in the operation of a lithium cell, these hydrophobic groups serve to repel water molecules.

In a first example, ethanol is used as providing hydrophobic ethoxy groups ($—OC_2H_5$) for replacing hydroxyl groups on the surfaces of lithium titanate particles. The chemical reaction of ethanol with representative hydroxyl groups on the surface of a single LTO particle is illustrated in FIG. 2 which provides an enlarged schematic illustration of the reaction of ethanol with four sites of hydroxyl groups. Each actual LTO particle in a volume of particles to be processed, exposed to ambient air or the like, would have many such hydroxyl group sites substantially covering the surfaces of each particle.

In the left side of FIG. 2, a generally spherical $Li_4Ti_5O_{12}$ particle is schematically illustrated as having four equally-spaced (90° spacing) titanium sites on a planar sectional circumference of its surface. Of course, an actual LTO particle would have many, many such titanium atom sites exposed on the surface of each particle and such titanium atoms would likely be coupled with oxygen atoms in the crystalline particle. In order to present an illustration of the chemistry of the subject surface modification process, only a few of the surface titanium sites are schematically enlarged and depicted as labeled dot-filled semicircles.

Hydroxyl groups (depicted as OH) are depicted as chemically bonded to the surface titanium sites. It is believed that a water molecule reacting at a titanium atom site provides a hydroxyl group on the titanium atom and a hydrogen atom on an adjacent oxygen atom in the surface crystal structure of the LTO particle.

Four water molecules ($H_2O$) are also schematically depicted as being simply physically adsorbed to the surface of the LTO particle.

In this portion of FIG. 2, the contact of ethanol vapor or liquid ethanol with the surface of the LTO particle is indicated by the formula, $C_2H_5OH$, and directional arrow. The directional reaction-indicating arrow in the center of FIG. 2, and the schematic illustration of the LTO particle on the right side of FIG. 2, illustrate the effect of suitable contact of the ethanol with the surface of each LTO particle. Adsorbed water molecules are removed from the surface of the LTO particle and ethanol molecules have reacted with the four surface-illustrated hydroxyl groups to replace them with four ethoxy groups and to form water as a chemical reaction by-product. As stated these reactions, illustrated schematically in FIG. 2, would occur many times on the surface of each $Li_4Ti_5O_{12}$ particle and the surface of each LTO particles would be substantially coated with pendant ethoxy groups. Practices for contacting a selected volume of LTO particles with ethanol or other suitable alcohol may be practiced in accordance with the following examples.

In a first example, a volume of LTO particles are simply mixed in a pure liquid alcohol such as, for example, methanol, ethanol, a propanol, or a butanol. In accordance with normal material handling practices the particles will have been exposed to normal ambient atmospheric conditions with water-containing air. The liquid alcohol wets the surfaces of the LTO particles, displacing adsorbed water and reacting with hydroxyl groups on the surfaces of the particles. This reaction by for example, ethanol, may be conducted at temperatures ranging from 0° C. to 200° C. at predetermined compatible pressures in the range of one to three bar. For example, liquid ethanol could be used to wet and react with the surfaces of the LTO particles at a temperature of 50° C. and at a pressure of one bar. The particles are filtered or otherwise suitably removed from the liquid alcohol and the LTO particles are then placed, for example, in a vacuum oven, to remove all liquid alcohol and water from the surfaces of the particles. The particles may be heated in the oven to a suitable determined temperature, for example up to about 200° C. at pressures up to three bar.

In a similar related process, LTO particles may be placed and distributed in and along an enclosed tube or channel. A mixture of aliphatic alcohol vapor, which may be diluted with a dry inert gas, is flowed over the particles at a selected temperature up to for example about 200° C. at pressures up to three bar. At the completion of the reaction of the LTO particles with the alcohol, a flow of heated inert gas at a reduced pressure may be used to remove residual alcohol.

The dried alcohol-treated LTO particles are ready for processing as an active electrode material for forming an anode in a lithium-ion or other lithium anode using cell or battery. The LTO particles with their coating of pendant alkoxy groups may, for example, be mixed with a suitable minor portion of carbon black particles or other suitable conductive particles, and further mixed with a solution or dispersion of a suitable polymeric binder such as polyvinylidene difluoride (PVDF) in an anhydrous solvent such as N-methyl-2-pyrrolidone (NMP). The mixture of particulate anode material constituents may then be applied as a suitably thick layer over, for example, a copper current collector foil. The binder is suitably treated and the NMP solvent removed to complete the formation of the porous electrode material. The anode structure may be utilized with a complementary cathode structure, interposed separator, and infiltrated anhydrous electrolyte solution to assemble a cell or a desired number of interconnected cells in a battery structure.

Treatment of LTO Particles with Sulfur Containing Compounds.

LTO particles with surface OH groups may be treated with solutions of compounds of sulfenic acid (R—S—OH), sulfinic acid (R—SO—OH), or sulfonic acid (R—S($=$O)$_2$—OH or R—SO$_3$H). The OH groups of these acids react with the hydrogen ions (H+) of the OH groups on the surfaces of the LTO particles to form pendant hydrophobic groups on the LTO particles and water as a by-product.

Suitable compounds of sulfenic acid, for example, include methyl sulfenic acid (CH$_3$SOH), propyl sulfenic acid (C$_3$H$_8$SOH) and the like.

Suitable compounds of sulfinic acid include phenyl sulfinic acid (C$_6$H$_5$—SO—OH), hydroxymethyl sulfinic acid (HOCH$_2$—SO—OH), and the like.

Suitable compounds of sulfonic acid include toluene sulfonic acid (C$_7$H$_7$SO$_3$H), taurine (C$_2$H$_4$NH$_2$SO$_3$H), and the like.

A solution of the sulfur-containing acid compound is dissolved in a non-aqueous solvent such as benzene, toluene, or furan and the solution used to react with hydroxyl groups on the surfaces of a volume of LTO particles. At the completion of the surfaces reactions, the LTO particles are filtered or removed from the solution of sulfur-containing acid. The LTO particles are rinsed with fresh solvent and filtered. The LTO particles are then placed, for example, in a vacuum oven, to remove residual solvent from the surfaces of the particles. The particles may be heated in the oven to a suitable determined temperature, for example up to about 200° C. at pressures up to three bar.

The surfaces of the LTO particles are now coated with pendant hydrophobic groups comprising the selected sulfur acid moiety and the attached organic alkyl, aromatic, and or amino-alkyl groups. The treated LTO particles may be processed, as described above, into porous, resin-bonded particulate active anode material layers.

Treatment of LTO Particles with Silane Coupling Agents.

It is preferred to use silane coupling agents characterized by the formula Y$_{4-a}$Si(OX)$_a$, where a has a value of 1-3, where X and Y may be alkyl groups selected such that one alkoxy group (OX) reacts with a hydroxyl group on the surface of a LTO particle and the remaining OX and Y groups serve to block water molecules from access to the surface of the particle. Examples of such compounds are hexadecyltrimethoxysilane, methyltrimethoxysilane, dimethyldimethoxysilane, and methoxytrimethylsioxane.

Figure 3:
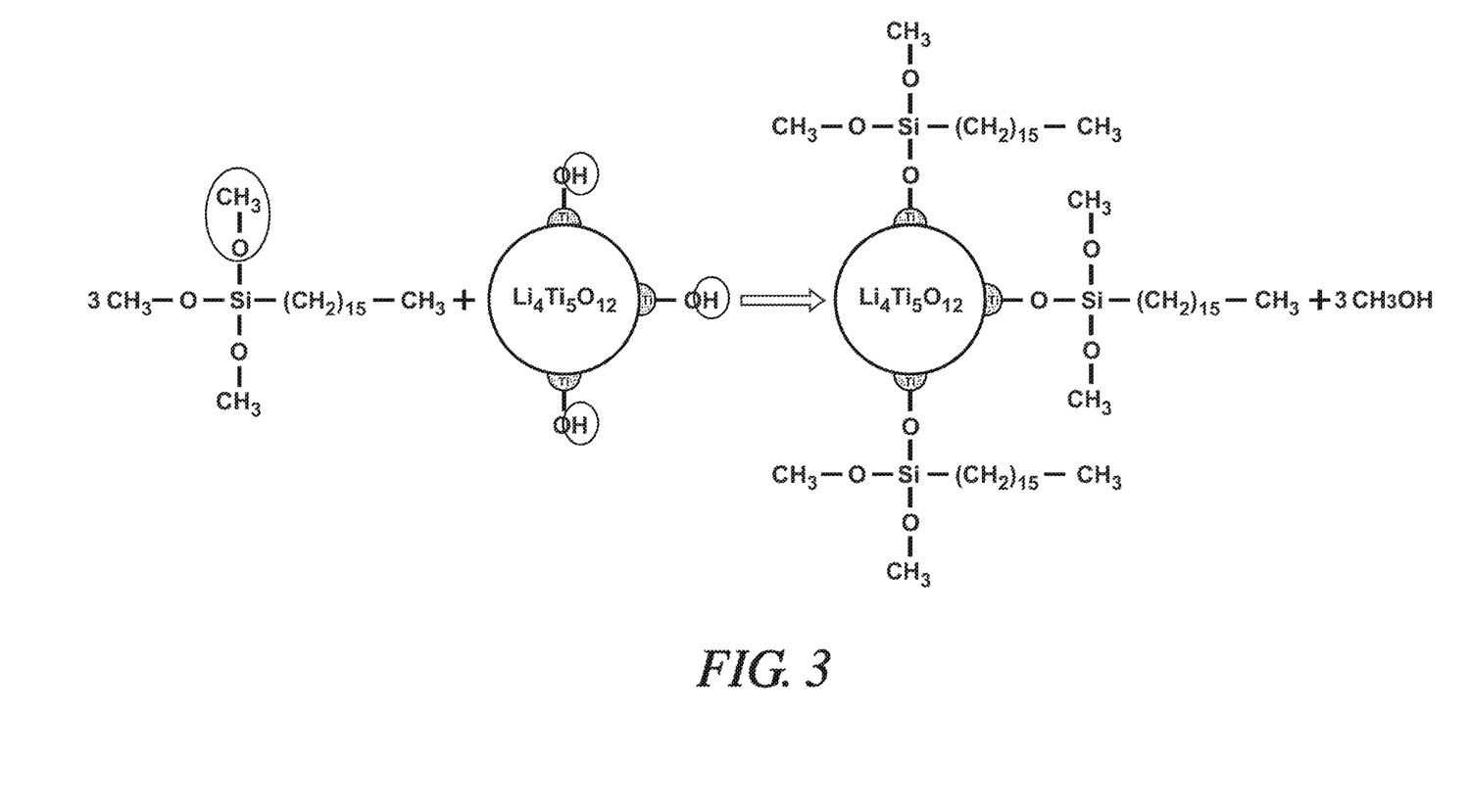
FIG. 3 is an enlarged schematic illustration of the chemical treatment of the surface of a powder particle of lithium titanate with a silane coupling agent, hexadecyltrimethoxy silane, to form pendant oxy-silane groups at a few schematically illustrated OH sites on the surface of the powder particle. The surface of each LTO particle contains many OH groups which react with a methoxy group on the silane coupling agent to release methanol and to form many pendant surface silane groups. When such treated lithium titanate powder is employed in the operation of a lithium cell, these hydrophobic groups serve to repel water molecules.

On the left side of FIG. 3 a generally spherical Li$_4$Ti$_5$O$_{12}$ particle is schematically illustrated as having three spaced-apart titanium sites on a planar circumference of its surface. The titanium sites are illustrated schematically as Ti-labeled, dot-filled semi-circles on the circumference of the Li$_4$Ti$_5$O$_{12}$ spherical particle. Again, each LTO particle would have a very large number of titanium sites on its crystalline surface. FIG. 3 is configured to illustrate the chemistry of the surface modification process. Hydroxyl groups (depicted as OH) are depicted as chemically bonded to the titanium sites on the surface of the LTO particle. At the far left side of FIG. 3 is a schematic two-dimensional representation of a molecule of hexadecyltrimethoxysilane. Three such silane molecules are required to react with the hydroxyl groups on the three schematically-illustrated titanium sites. A methoxy group (e.g., the circled methoxy group) on each silane molecule reacts with a proton (circled H atom) on a hydroxyl group on the LTO particle.

In FIG. 3, the reaction of hexadecyltrimethoxysilane with the hydroxyl groups on the surface titanium sites of the LTO particle is indicated by the schematic structural formula, and directional arrow. The open directional arrow in the center of FIG. 3 and the schematic illustration of the LTO particle on the right side of FIG. 3 illustrate the effect of suitable contact of the silane coupling agent with the surface of each LTO particle. A methoxy group from the molecule of the silane coupling agent has reacted with the hydrogen atom on the hydroxyl group to attach the silane coupon agent to the titanium site. Methanol is removed as a byproduct, and the hexadecyl group and the remaining methoxy groups of the silane coupling agent serve as a hydrophobic blocking moiety on the surface of the LTO particle. This reaction, as illustrated schematically in FIG. 3, depicts three such reactions on the surface of the LTO particle. But the reaction occurs many times on the surfaces of each of the LTO particles to provide suitable coatings of the silane coupling agents to shield the LTO particles from water molecules when the particles have been incorporated into anode electrodes in lithium-ion cells.

The reaction of such silane coupling agents with a volume of LTO particles may be conducted as follows.

A solution of a selected silane coupling agent is formed in a non-aqueous solvent such as benzene, toluene, or furan and the solution used to react with hydroxyl groups on the surfaces of a volume of LTO particles. The reaction of the silane coupling agent with the hydroxyl groups on the surfaces of the LTO particles may require modest heating over a predetermined period of time. The by-product alcohol may be separated and recovered from the solution of the coupling agent. At the completion of the reaction the surface-coated LTO particles are filtered or removed from the solution of the silane coupling agent. The LTO particles are rinsed with fresh solvent and filtered. The LTO particles are then placed, for example, in a vacuum oven, to remove residual solvent from the surfaces of the particles. The particles may be heated in the oven to a suitable determined temperature, for example up to about 200° C. at pressures up to three bar to promote removal of the solvent.

The surfaces of the LTO particles are now coated with pendant hydrophobic groups comprising the selected silicon-based silane moiety and the attached organic alkyl and alkoxy groups. The silane coupling agent treated LTO particles may be processed, as described above, into porous, resin-bonded particulate active anode material layers.

Treatment of LTO Particles with Titanate Coupling Agents.

A first example of suitable titanate coupling agents are represented by the formula, Ti(OX)$_4$, where X represents an alkyl group containing 1-6 carbon atoms. Tetrabutyl titanate, (C$_4$H$_9$O)$_4$Ti, is an example of such a coupling agent. This alkyl titanate has four alkoxy groups, any one of which may react with a hydroxyl group on the surface of an LTO particle to couple a hydrophobic titanate moiety, —O—Ti (OC$_4$H$_9$)$_3$, to the surface of the particle and to simultaneously release a molecule of butyl alcohol. The use of tetrabutyl titanate to react with LTO particles with pendant hydroxyl groups is illustrated schematically in FIG. 4.

Figure 4:
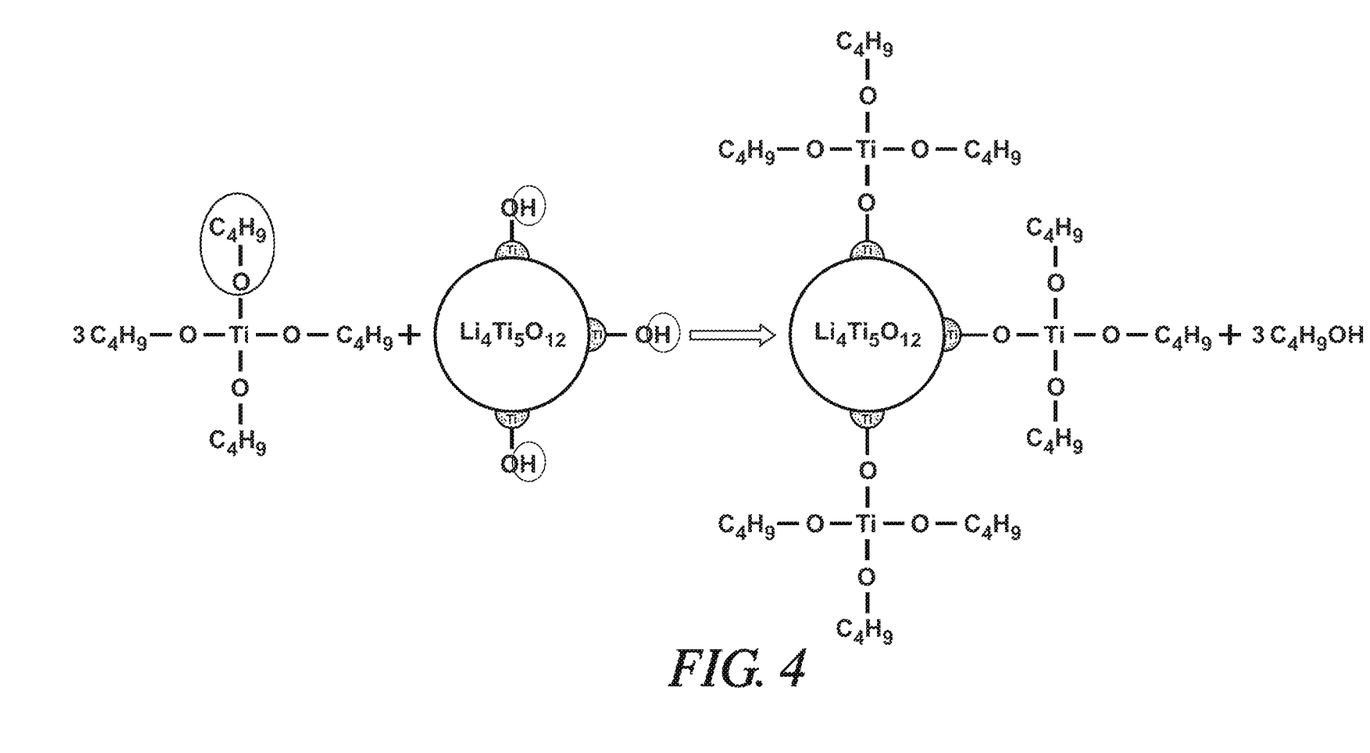
FIG. 4 is an enlarged schematic illustration of the chemical treatment of the surface of a powder particle of lithium titanate with a titanate coupling agent, tetra butoxy titanate, to form pendant surface titanate groups at a few schematically-illustrated OH sites on the surface of the powder particle. The surface of each LTO particle contains many OH groups which react with butoxy groups on the tetra-butoxy titanate to release butyl alcohol and to form many butoxy groups which do not react with any water which in the operation of a lithium cell containing the treated lithium titanate powder as an electrode material.

As depicted in FIG. 4, a butoxy group (circled in the two-dimensional representation of a molecule of $(C_4H_9O)_4Ti$) from each of three titanate molecules reacts with a circled hydrogen atom on three schematically illustrated hydroxyl groups on titanium atoms on a LTO particle. As indicated at the right side of the reaction arrow in FIG. 4, a hydrophobic titanate moiety, —O—Ti(OC$_4$H$_9$)$_3$, is now bonded to the LTO particle in place of each of the three original hydroxyl groups and three molecules of recoverable butyl alcohol are released.

Thus, when LTO particles with pendant OH groups are contacted with a suitable solution of this tetra-alkyl titanate, pendant tributyl titanate groups are attached to titanium sites on the surface of each particle, providing hydrophobic alkyl titanate groups that block water molecules from access to the LTO particles when they are employed as active anode material in a lithium cell.

Other suitable titanate coupling agents include one to three alkoxy groups attached to a tetravalent titanium atom and other alkyl groups, without an oxygen atom, attached to the titanium atom. Examples include $Ti(OX)_3Y$, $Ti(OX)_2YR_1$, $Ti(OX)YR_1R_2$, where X and Y are alkyl groups and $R_1$ is an alkyl group and $R_2$ is an alkyl group.

The reaction of such titanate coupling agents with a volume of LTO particles may be conducted as follows.

A solution of a selected titanate coupling agent is formed in a non-aqueous solvent such as benzene, toluene, or furan and the solution used to react with hydroxyl groups on the surfaces of a volume of LTO particles. The reaction of the titanate coupling agent with the hydroxyl groups on the surfaces of the LTO particles may require modest heating over a predetermined period of time. The by-product alcohol may be separated and recovered from the solution of the coupling agent. At the completion of the reaction, the surface-coated LTO particles are filtered or removed from the solution of the titanate coupling agent. The LTO particles are rinsed with fresh solvent and filtered. The LTO particles are then placed, for example, in a vacuum oven, to remove residual solvent from the surfaces of the particles. The particles may be heated in the oven to a suitable determined temperature, for example up to about 200° C. at pressures up to three bar to promote removal of the solvent.

The surfaces of the LTO particles are now coated with pendant hydrophobic groups comprising the selected titanium-based titanate moiety and the attached organic alkyl and alkoxy groups. The titanate coupling agent treated LTO particles may be processed, as described above, into porous, resin-bonded particulate active anode material layers for lithium cells.

Thus, at least four different types of reactants and/or coupling agents are disclosed and utilized for reaction with hydroxyl group-containing surfaces of lithium titanate particles intended for use as active anode particles in a lithium-ion cell or similar lithium cell. Each surface reactant is selected to react with the surface hydroxyl groups and to replace them with hydrophobic organic alkyl groups, or the equivalent, that block access of water molecules to the surfaces of the LTO particles when they are receiving (intercalation) and releasing (de-intercalation) lithium ions in the anhydrous environment of a lithium electrochemical cell. By blocking access of water to the particulate LTO anode material, gas generation is reduced or eliminated in the operation of the cell.

Examples of practices of the LTO surfaces coating methods are described for purposes of illustration. Such illustrations are not intended to limit the scope of the claimed invention.

The invention claimed is:

1. A method of preparing lithium titanate ($Li_4Ti_5O_{12}$) particles, characterized by the presence of hydroxyl groups on the surfaces of the particles, for use as anode material particles in an electrochemical cell with an anhydrous electrolyte, the preparation of the lithium titanate particles being performed to replace the hydroxyl groups on the surfaces of the particles with hydrophobic groups for isolating the lithium titanate particles from water molecules produced as a contaminant in the operation of the electrochemical cell; the method comprising:

reacting the hydroxyl groups on the surfaces of the lithium titanate particles with molecules of a compound selected from the group consisting of an alkanol, a sulfur-containing acid, a tetravalent silicon-containing compound, and a tetravalent titanium-containing compound, the selected compound containing hydroxyl groups or alkoxy groups or both alkyl groups and alkoxy groups, such that the reaction of the molecules of the selected compound with the hydroxyl groups on the lithium titanate particles produces water or an alcohol as a product removable from the lithium titanate particles, and molecular moieties of the remainder of the molecules of the selected compound are attached to the surfaces of the lithium titanate particles in place of the hydroxyl groups, the attached molecular moieties containing alkoxy groups or a combination of alkoxy groups and alkyl groups such that the remaining molecular moieties attached to the surfaces of the lithium titanate particles serve as barriers to water contamination when the lithium titanate particles are subsequently placed and used in an electrochemical cell, and removing any residual selected compound and any residual water from the surface of the lithium titanate particles.

2. The method of claim 1 wherein the selected compound is an alkanol having one to four carbon atoms such that the molecules of alkanol react with the hydroxyl groups on the surfaces of the lithium titanate particles to form water as a by-product and to replace the hydroxyl groups with alkoxy groups to serve as barriers to water contamination.

3. The method of claim 2 wherein the alkanol is applied as a liquid to contact the surfaces of the lithium titanate particles to replace the hydroxyl groups with alkoxy groups, and excess liquid alcohol and by-product water are then removed from the alkoxy-coated lithium titanate particles.

4. The method of claim 2 wherein the alkanol is applied as a vapor to contact the surfaces of the lithium titanate particles to replace the hydroxyl groups with alkoxy groups, and the alcohol vapor and by-product water are then removed from the alkoxy-coated lithium titanate particles.

5. The method of claim 1 wherein the selected compound is a sulfur-containing acid selected from the group consisting of a sulfinic acid, a sulfenic acid, and a sulfonic acid, the sulfur-containing acid having a hydroxyl group, such that the sulfur-containing acid reacts with the hydroxyl groups on the surfaces of the lithium titanate particles to form water as a by-product and to replace the hydroxyl groups with a sulfur-containing moiety with at least one of alkyl groups, aromatic groups, and alkyl amino groups to serve as barriers to water contamination.

6. The method of claim 5 wherein the sulfur containing acid compound is dissolved in a non-aqueous solvent and the solution is applied to the surfaces of the lithium titanate particles to replace the hydroxyl groups with the sulfur-containing moiety, and any residual solution and any residual water are removed from the lithium titanate particles.

7. The method of claim 1 where the selected compound is a tetravalent silicon-containing compound with one to four alkoxy groups and the remainder alkane groups, such that an alkoxy group of the silicon-containing compound reacts with the hydroxyl groups on the surfaces of the lithium titanate particles to form an alcohol as a by-product and to replace the hydroxyl groups with a tetravalent silicon-containing moiety with alkoxy groups or a combination of alkoxy groups and alkyl groups to serve as barriers to water contamination.

8. The method of claim 7 wherein the tetravalent silicon-containing compound is a silane selected from the group consisting of hexadecyltrimethoxysilane, methyltrimethoxysilane, dimethyl dimethoxysilane, and methoxytrimethylsilane.

9. The method of claim 7 wherein the silicon-containing compound is dissolved in a non-aqueous solvent and the solution is applied to the surfaces of the lithium titanate particles to replace the hydroxyl groups with the tetravalent silicon-containing moiety, and any residual solution and any residual water are removed from the lithium titanate particles.

10. The method of claim 1 where the selected compound is a tetravalent titanium-containing compound with one to four alkoxy groups and the remainder alkane groups, such that alkoxy groups of the titanium-containing compound react with the hydroxyl groups on the surfaces of the lithium titanate particles to form an alcohol as a by-product and to replace the hydroxyl groups with a tetravalent titanium-containing moiety with alkoxy groups or a combination of alkoxy groups and alkyl groups to serve as barriers to water contamination.

11. The method of claim 10 wherein the tetravalent titanium-containing compound is a compound represented by one of $Ti(OX)_4$, $Ti(OX)_3Y$, $Ti(OX)_2YR_1$, $Ti(OX)YR_1R_2$, where X and Y are alkyl groups and $R_1$ is an alkyl group and $R_2$ is an alkyl group containing 1-6 carbon atoms.

12. The method of claim 10 wherein the tetravalent titanium-containing compound is dissolved in a non-aqueous solvent and the solution is applied to the surfaces of the lithium titanate particles to replace the hydroxyl groups with the tetravalent titanium-containing moiety, and any residual solution and any residual water are removed from the lithium titanate particles.

13. A method of preparing lithium titanate ($Li_4Ti_5O_{12}$) particles, characterized by the presence of hydroxyl groups on the surfaces of the particles, for use as anode material particles in an electrochemical cell with an anhydrous electrolyte, the preparation of the lithium titanate particles being performed to replace the hydroxyl groups on the surfaces of the particles with hydrophobic groups for isolating the lithium titanate from water molecules produced as a contaminant in the operation of the electrochemical cell; the method comprising:

reacting the hydroxyl groups on the surfaces of the particles with an aliphatic alkanol having one to four carbon atoms, the reaction of the aliphatic alkanol with the hydroxyl groups on the lithium titanate particles producing water as a product removable from the particles, and alkoxy groups attached to the surfaces of the lithium titanate particles in place of the hydroxyl groups, the attached alkoxy groups attached to the surfaces of the lithium titanate particles being selected to serve as barriers to water reaction with the lithium titanate particles when they are subsequently placed as an anodic electrode and used in an electrochemical cell employing an anhydrous electrolyte and in which the lithium titanate particles are to be used to repeatedly intercalate and de-intercalate lithium ions in the charging and discharging of the cell, and removing any residual aliphatic alkanol and any residual water from the surface of the lithium titanate particles.

14. The method of claim 13 wherein the aliphatic alkanol is applied as a liquid to contact the surfaces of the lithium titanate particles to replace the hydroxyl groups with alkoxy groups, and excess liquid alcohol and by-product water are then removed from the alkoxy-coated lithium titanate particles.

15. The method of claim 13 wherein the aliphatic alkanol is applied as a vapor to contact the surfaces of the lithium titanate particles to replace the hydroxyl groups with alkoxy groups, and the alcohol vapor and by-product water are then removed from the alkoxy-coated lithium titanate particles.

16. A method of preparing lithium titanate ($Li_4Ti_5O_{12}$) particles, characterized by the presence of hydroxyl groups on the surfaces of the particles, for use as anode material particles in an electrochemical cell with an anhydrous electrolyte, the preparation of the lithium titanate particles being performed to replace the hydroxyl groups on the surfaces of the particles with hydrophobic groups for isolating the lithium titanate from water molecules produced as a contaminant in the operation of the electrochemical cell; the method comprising:

reacting the hydroxyl groups on the surfaces of the particles with molecules of a compound selected from the group consisting of a tetravalent silicon-containing compound and a tetravalent titanium-containing compound, the selected compound containing alkoxy groups or both alkoxy groups and alkyl groups, such that the reaction of the selected compound with the hydroxyl groups on the lithium titanate particles produces an alcohol as a product removable from the particles, and molecular moieties of the remainder of the molecules of the selected compound are attached to the surfaces of the lithium titanate particles in place of the hydroxyl groups, the remaining molecular moieties containing alkoxy groups or a combination of alkoxy groups and alkyl groups such that the remaining molecular moieties attached to the surfaces of the lithium titanate particles can serve as barriers to water contamination when the lithium titanate particles are subsequently placed and used in an electrochemical cell, and removing any residual selected compound and any residual alcohol from the surfaces of the lithium titanate particles.

17. The method of claim 16 wherein the tetravalent silicon-containing compound is a silane selected from the group consisting of hexadecyltrimethoxysilane, methyltrimethoxysilane, dimethyldimethoxysilane, and methoxytrimethylsilane.

18. The method of claim 16 wherein the silicon-containing compound is dissolved in a non-aqueous solvent and the solution is applied to the surfaces of the lithium titanate particles to replace the hydroxyl groups with a tetravalent silicon-containing moiety with alkoxy groups or a combination of alkoxy groups and alkyl groups, and any residual solution and any residual water are removed from the lithium titanate particles.

19. The method of claim 16 where the selected compound is a tetravalent titanium-containing compound with one to four alkoxy groups and the remainder alkane groups, such that alkoxy groups of the titanium-containing compound react with the hydroxyl groups on the surfaces of the lithium titanate particles to form an alcohol as a by-product and to replace the hydroxyl groups with a tetravalent titanium-containing moiety with alkoxy groups or a combination of alkoxy groups and alkyl groups to serve as barriers to water contamination.

20. The method of claim 16 wherein the tetravalent titanium-containing compound is a compound represented by one of $Ti(OX)_4$, $Ti(OX)_3Y$, $Ti(OX)_2YR_1$, $Ti(OX)YR_1R_2$, where X and Y are alkyl groups and $R_1$ is an alkyl group and $R_2$ is an alkyl group containing 1-6 carbon atoms.

* * * * *